United States Patent
Nagel et al.

(10) Patent No.: US 10,012,608 B2
(45) Date of Patent: Jul. 3, 2018

(54) METHOD FOR MANUFACTURING AN INDUCTIVE CONDUCTIVITY SENSOR AND AN INDUCTIVE CONDUCTIVITY SENSOR

(71) Applicant: Endress + Hauser Conducta Gesellschaft für Mess- und Regeltechnik mbH + Co. KG, Gerlingen (DE)

(72) Inventors: Thomas Nagel, Wilsdruff (DE); Andre Pfeifer, Schkopau (DE); Christian Fanselow, Geringswalde (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 374 days.

(21) Appl. No.: 14/817,553

(22) Filed: Aug. 4, 2015

(65) Prior Publication Data
US 2016/0061760 A1   Mar. 3, 2016

(30) Foreign Application Priority Data
Aug. 7, 2014   (DE) .......................... 10 2014 111 266

(51) Int. Cl.
*G01N 27/02* (2006.01)
*B23K 20/10* (2006.01)
(Continued)

(52) U.S. Cl.
CPC ........... *G01N 27/025* (2013.01); *B23K 20/10* (2013.01); *H01F 27/027* (2013.01); *B23K 2201/42* (2013.01)

(58) Field of Classification Search
CPC .... B23K 2201/42; B23K 20/10; H01F 27/027
(Continued)

(56) References Cited

U.S. PATENT DOCUMENTS 3,038,358 A *   6/1962   Jones ................... B23K 20/106
                                                    228/1.1
4,259,419 A *   3/1981   Uba ........................ B29C 65/08
                                                    156/580.1
(Continued)

FOREIGN PATENT DOCUMENTS

CN           2593202 Y      12/2003
CN         102590634 A       7/2012
(Continued)

*Primary Examiner* — Melissa Koval
*Assistant Examiner* — Courtney McDonnough
(74) *Attorney, Agent, or Firm* — Christopher R. Powers; PatServe

(57) ABSTRACT

A method for manufacturing an inductive conductivity sensor, with coils on both sides of a circuit board are placed surrounding an opening of the circuit board. The circuit board with the coils is inserted into a housing, wherein a sleeve is inserted in the housing through a second opening of the housing through the opening of the circuit board out to a first opening. The first opening, the second opening and the opening of the circuit board are aligned with one another, wherein the sleeve includes a first end section and a second end section and the sleeve is inserted with the first end section first in the housing, and wherein the sleeve is welded with the housing by means of a sonotrode by ultrasonic welding. The first end section of the sleeve is welded with the housing and with a counterpart inserted into the first opening. The invention relates further to an inductive conductivity sensor.

19 Claims, 4 Drawing Sheets

(51) Int. Cl.
*H01F 27/02* (2006.01)
*B23K 101/42* (2006.01)

(58) Field of Classification Search
USPC .......................................... 324/654
See application file for complete search history.

(56) References Cited

U.S. PATENT DOCUMENTS

| | | | |
|---|---|---|---|
| 2003/0151145 A1* | 8/2003 | Hesse | H01L 21/563 257/778 |
| 2008/0028593 A1 | 2/2008 | Friedrichs et al. | |
| 2012/0098550 A1* | 4/2012 | Fanselow | G01D 5/20 324/654 |

FOREIGN PATENT DOCUMENTS

| | | |
|---|---|---|
| CN | 103869174 A | 6/2014 |
| DE | 19508221 C1 | 9/1996 |

* cited by examiner

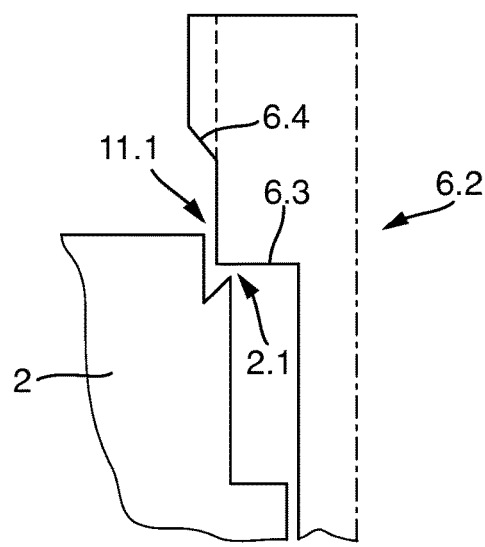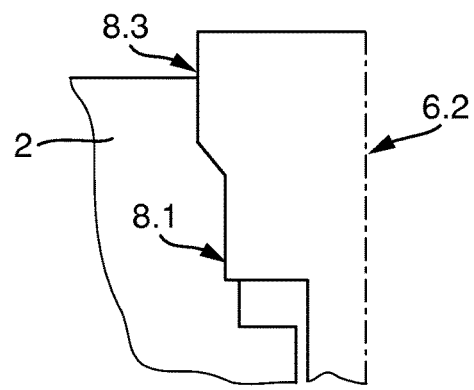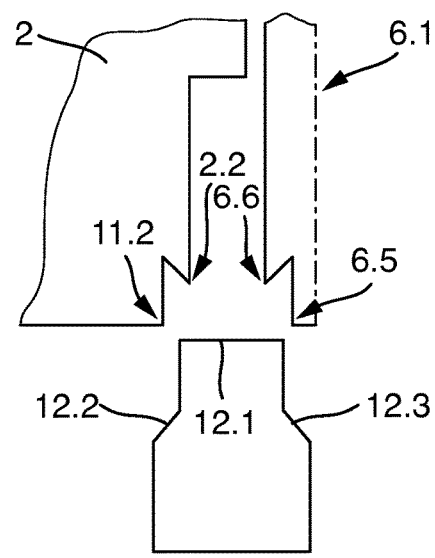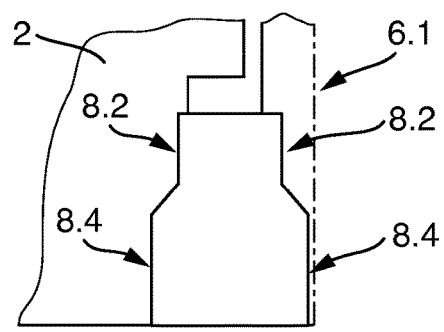
Fig. 2a                    Fig. 2b

METHOD FOR MANUFACTURING AN INDUCTIVE CONDUCTIVITY SENSOR AND AN INDUCTIVE CONDUCTIVITY SENSOR

TECHNICAL FIELD

The invention relates to a method for manufacturing an inductive conductivity sensor and to an inductive conductivity sensor produced by such a method.

BACKGROUND DISCUSSION

Inductive conductivity sensors serve in a large number of applications in laboratory and process measurements technology for registering the conductivity of a liquid medium. They are used preferably where large measuring ranges and high chemical or thermal loadings occur. This is the case, for example, in a large number of industrial chemical processes and also in hot steam sterilization methods, which are frequently applied in foods technology due to the high hygiene requirements.

As a result of the mentioned requirements, frequently high performance plastics are used. Polyetheretherketone (abbreviated PEEK) is an example of a high temperature resistant, thermoplastic, synthetic material and is a member of the group, polyaryletherketones. Polyetheretherketone (PEEK) is a partially crystalline thermoplastic with high tensile—and bending strength, high impact toughness, high fatigue strength, high chemical resistance and is only difficultly burnable.

An inductive conductivity sensor includes a transmitting coil and a receiving coil, which, as a rule, are embodied as ring coils, also referred to as toroidal coils. Such a conductivity sensor functions as a type of double transformer, wherein the transmitting and receiving coils are inserted so far into the medium that a closed electrical current path can form extending through the medium and passing through the transmitting and receiving coils. When the transmitting coil is excited with an alternating voltage signal as an input signal, it produces a magnetic field, which induces in the closed path through the medium passing through the coils an electrical current, whose strength depends on the electrical conductivity of the medium. Since this alternating electrical current in the medium brings about, in turn, a variable magnetic field surrounding it, an alternating electrical current is induced in the receiving coil as an output signal. This alternating electrical current, respectively a corresponding alternating voltage, delivered from the receiving coil as an output signal is a measure for the electrical conductivity of the medium.

For feeding the transmitting coil with an alternating voltage, an inductive conductivity sensor includes a driver circuit connected with the transmitting coil. For registering the output signal of the receiving coil, the conductivity sensor includes, moreover, electrically connected with the receiving coil, a receiving circuit, which is embodied to output the registered measurement signal, in given cases, conditioned by the receiving circuit, to a sensor electronics, which serves to process the measurement signal further and, in given cases, to digitize it. Frequently, conductivity sensors are embodied as measuring probes at least sectionally immersible in the medium. Such measuring probes include a housing, in which the transmitting and receiving coils, in given cases, the driver circuit and the receiving circuit as well as other circuit parts assembled with the transmitting and receiving circuit into a sensor circuit, are accommodated. The measuring probe is connected in such an embodiment with a removed, superordinated unit, for example, a display unit, a measurement transmitter, or a computer. The superordinated unit can be embodied both for energy supply of the measuring probe as well as also for data communication with the measuring probe. The sensor circuit optionally contained in the measuring probe can be embodied to forward the further processed, in given cases, digitized, measurement signal to the superordinated unit. The corresponding measured value can be displayed via the superordinated unit by means of a display system or output via a data interface.

The coils of the inductive conductivity sensors can be provided with a housing in various ways. In one known method, a coil component is formed, in the case of which the coils are, first of all, in a complex method, introduced into a separate coil housing and then injection molded around, in this coil housing, with plastic. The so produced assembly is then inserted into a sensor housing. The creating of the separate coil housing is necessary, in order to protect the coils in the injection molding from the high injection pressures and very high temperatures during the injection procedure. Since the coils are very sensitive to pressure and temperature, there is present in this processing besides a high preparation—and assembly effort for the coil component a high rejection risk.

In the case of a known sensor, two coils are arranged, in each case, on a side of a circuit board and then the prefabricated circuit board is inserted into the sensor housing. The circuit board includes, in such case, an opening, in order to position the coils in the form of toroidal coils. After the insertion of the circuit board into the sensor housing, the housing is sealed by a sleeve, which is inserted through a wall of the housing into the housing and guided through the opening of the circuit board. The two ends of the sleeve are, in such case, adhered to the housing at the interfaces with such. The inner space of the sensor housing is, in this connection, filled with a potting compound. Besides the preparation effort for the adhesive locations, which must be cleaned before the adhesion process, also a rework of the adhesive at the transition locations is necessary. The adhesive gap, which forms between sleeve and housing, has a different coefficient of thermal expansion than the housing, wherein in the case of temperature changes during use of the inductive sensor the adhesive gap can be damaged. Moreover, the adhesive has a lesser chemical durability than the plastic. For manufacturing the two separate adhesive locations, a complex handling is necessary, which lengthens the time required for the procedure.

Known from German Patent DE 10 2010 042 832 is a process utilizing ultrasonic welding.

The dissertation of Joachim Nehr with the title "Neuro-Fuzzy-Modellierung zur umfassenden Prozessüberwachung am Beispiel des Ultraschallschweißens von Kunststoffteilen (neuro-fuzzy modeling for comprehensive process monitoring in the example of ultrasonic welding of plastic parts)", Universität Stuttgart (University of Stuttgart), year 2011, describes the ultrasonic welding process in the following way:

An oscillatable system, composed of converter, booster and sonotrode, is caused to oscillate with longitudinal oscillations in the ultrasonic region by excitation by means of piezo elements in the converter. Typical oscillation frequencies are, in such case, 20, 30, 35 or 40 kHz, depending on machine manufacturer and size of the workpieces to be welded. The initial oscillation amplitude in the small range from about 6 to 13 μm—depending on oscillation frequency—is amplified by the booster (also called the amplitude transformer) and the sonotrode application—and material specifically by a factor in the range, 1-5. By mechanical coupling of the sonotrode, the oscillation is introduced into the workpiece. The oscillatory energy is absorbed by inner friction and boundary friction, whereupon the occurring heat leads to a local melting in the joint zone and thereby to connection of the two joint partners.

The process flow in the case of ultrasonic welding is divided into three phases:

1) The start, wherein the sonotrode acts on the components to be connected and the mechanical coupling occurs with a selectable force; 2) The actual welding phase, during which the oscillation produced by the converter is introduced into the component at a given force level and leads to melting and connecting of the components; and 3) The holding phase for cooling the melt arising in the welding until the solid weld seam forms.

Depending on separation between weld zone and sonotrode where the oscillation is being introduced, a distinction is drawn between near field and far field welding, wherein a separation of about 6 mm marks the border between the two types of welding. Far field welds can be performed best with stiff thermoplastics, since an upturning of the parts related to the welding force should be kept as small as possible or completely prevented. Due to the shear modulus and mechanical loss factor, most often, only amorphous synthetic materials are welded in the far field. Partially crystalline plastic materials, which, most often, have a marked damping rise already well below the melting temperature, should only be welded in the near field.

SUMMARY OF THE INVENTION

An object of the invention is to provide a method for manufacturing an inductive conductivity sensor, in the case of which the handling during the connecting process of the sleeve with the housing is simplified and, while avoiding a high preparation effort, a stable connection between sleeve and housing is achieved.

The object is achieved by a method wherein on both sides of a circuit board coils are placed surrounding an opening of the circuit board and the circuit board with the coils is inserted into a housing, wherein a sleeve is inserted into the housing through a second opening of the housing through the opening of the circuit board and out to a first opening, wherein the first opening, the second opening and the opening of the circuit board are aligned with one another, wherein the sleeve includes a first end section and a second end section and the sleeve is inserted with the first end section first into the housing, and wherein the sleeve is welded with the housing by means of a sonotrode by ultrasonic welding. The method is characterized in that the first end section of the sleeve is welded with the housing and with a counterpart inserted into the first opening. Thus, the parts can be welded, in each case, in the near field.

In an advantageous form of embodiment, the sleeve is welded in the second opening, respectively second end section, before the first end section is welded with the housing and counterpart.

In a preferred embodiment, a shear joint is used for forming a seam geometry of a first weld seam, wherein the housing includes a first wedge shaped profile, and the first wedge shaped profile serves for forming the first weld seam in the region of the second end section with a first planar area on the sleeve, wherein the sonotrode is applied on the side of the second end section.

In a preferred further development, a shear joint is used for forming a seam geometry of a second weld seam, wherein the housing includes a second wedge shaped profile, wherein the sleeve includes a third wedge shaped profile, and the second wedge shaped profile and the third wedge shaped profile serve for forming the second weld seam in the region of the first end section with a second planar area on the counterpart, wherein the sonotrode is applied on the side of the first end section.

Preferably, a shear joint is used for forming a seam geometry of a third weld seam, wherein the housing includes a first energy concentrator, which is called the first concentrator in the following, and the first concentrator serves for forming the third weld seam in the region of the second end section with an inclined area of the sleeve, wherein the sonotrode is applied on the side of the second end section.

A concentrator is in general a structural feature, which brings something together, focuses, respectively compacts. In the sense of this invention, "concentrator" means concentrated melting region, thus the region where, due to a certain structure and geometry, the material begins to melt due to the ultrasonic welding.

In an advantageous form of embodiment, a shear joint is used for forming a seam geometry of a fourth weld seam, wherein the housing includes a second concentrator and the sleeve includes a third concentrator, and the second concentrator and the third concentrator serve for forming the fourth weld seam in the region of the first end section with at least a first inclined area and a second inclined area of the counterpart, wherein the sonotrode is applied on the side of the first end section.

Preferably, at least one of the above described concentrators has a V-shaped profile with an acute angle between 90° and 60°, a triangular profile, a rectangular profile or a half round profile. In this way, the energy can be optimally in-coupled. In other words, the concentrator is formed by a V-shaped profile having an acute angle between 90° and 60°, a triangular profile, a rectangular profile or a half round profile. In the sense of this invention, the "concentrator" includes a first section having a minimum bearing surface on the workpiece to be welded and a second section. During the welding, the concentrator melts up to the second section.

In the sense of this invention, indeed, a distinction is made between a "concentrator" and a "wedge shaped profile". Nevertheless, the "wedge shaped profile" can also be embodied as a V-shaped profile having an acute angle between 90° and 60°, a triangular profile, a rectangular profile or a half round profile. In their embodiment, i.e. material, geometry and structure, the two can, thus, be equal and achieve, thus, also the same result.

Following the welding, there is thus obtained a single part, which is composed of two different portions. However, a single homogeneous part is not obtained. Thus, the weld seams are visible after the welding.

In an advantageous further development, welding proceeds in the time sequence, first weld seam, third weld seam, second weld seam, fourth weld seam, wherein the first weld seam and the third weld seam, respectively the second weld seam and and the fourth weld seam, are for a certain time simultaneously molten.

For preventing long heat up phases, welding occurs advantageously at room temperature.

In a preferred further development, the sleeve welded with the housing is further worked, especially rounded, in the first end region and/or in the second end region. Thus, the conductivity sensor manufactured with the method then meets hygienic requirements. Possibly present cavities, corners and edges are removed and the resulting body is burr free.

The object is further achieved by an inductive conductivity sensor, which is produced according to one of the above described methods.

Preferably, the housing, the sleeve and the counterpart comprise a partially crystalline thermoplastic, especially a polyether ketone, especially polyetheretherketone (PEEK).

Alternatively, the housing, the sleeve and the counterpart comprise an amorphous thermoplastic, especially a polysulfone, especially polyphenylene sulfone (PPSU).

In an advantageous further development, the second end section includes at least a first weld seam, and the first end section includes at least a second weld seam. The second weld seam 8.2 has two subsections.

In an additional advantageous further development, the second end section includes supplementally at least a third weld seam, and the first end section includes supplementally at least a fourth weld seam. The fourth weld seam has two subsections.

There are different options for ending the welding process, for instance, after expiration of a constant time, after travel of a constant path, after reaching a certain point, after consumption of a predetermined amount of energy, after a predetermined power or a combination of all of these. Preferably, welding is according to a constant path, i.e. the two components melt, for instance, always equally far into one another.

BRIEF DESCRIPTION OF THE DRAWINGS

The invention will now be explained in greater detail based on the appended drawing, the figures of which show as follows:

FIG. 2*a* shows the weld seam before welding;

FIG. 2*b* shows the weld seam after welding; and

DETAILED DESCRIPTION IN CONJUNCTION WITH THE DRAWINGS

Figures 1A, 1B:
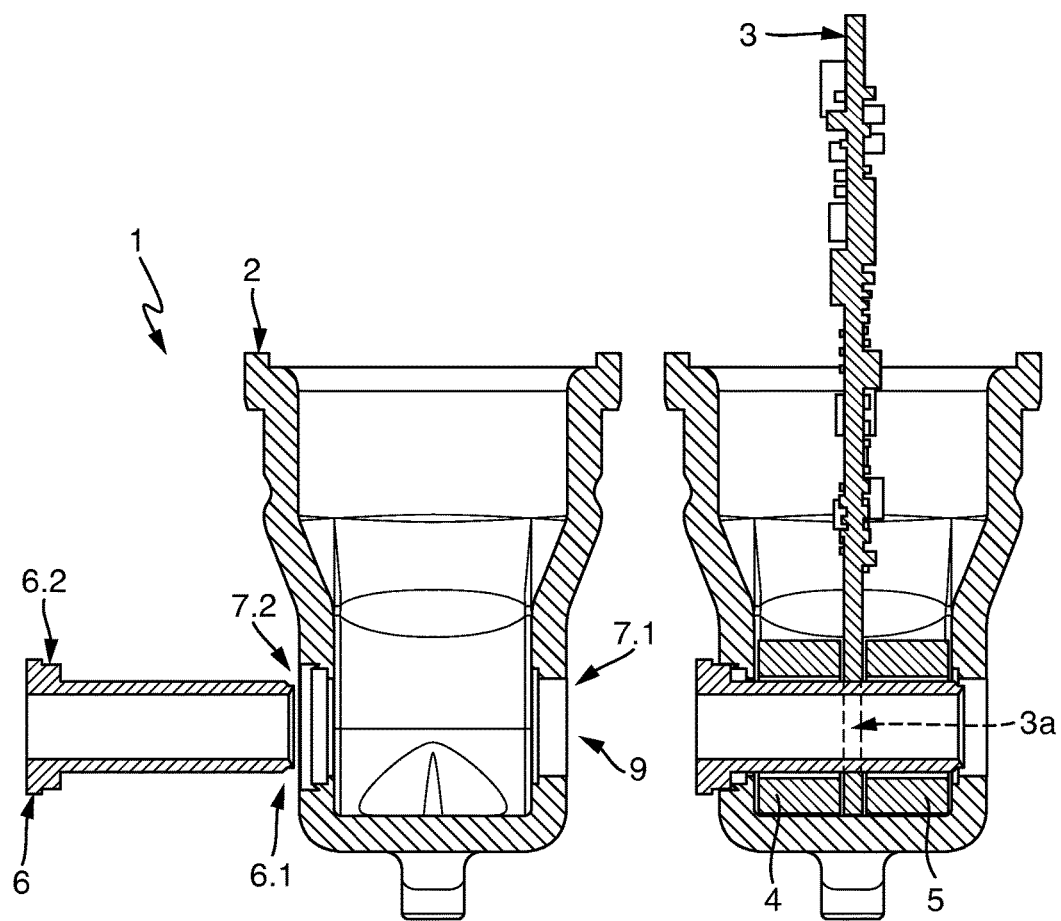
FIGS. 1*a*, 1*b*, 1*c*, 1*d* and 1*e* show the various stages in the manufacture of the conductivity sensor of the invention.
Figure 1C:
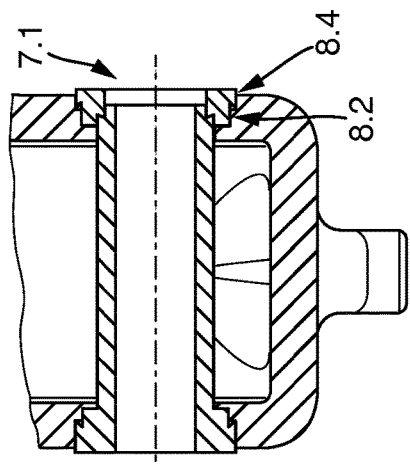

In the figures, equal features are provided with equal reference characters.

Shown in FIG. 1 in the form of FIGS. 1*a* to 1*e* are method steps for manufacturing a conductivity sensor. FIG. 1 shows a sensor module 1 of an inductive conductivity sensor 30 with a transmitting coil 4 and a receiving coil 5, which are accommodated in a housing 2. The transmitting coil 4 and the receiving coil 5 are arranged lying opposite one another on mutually facing away sides of a circuit card 3. The transmitting—and receiving coils 4, 5 embodied as rotationally symmetric, toroidal coils are, in this way, arranged coaxially lying behind one another. Circuit card 3 includes coil contacting, conductive traces (not shown), which connect the transmitting coil 4 with a driver circuit and the receiving coil 5 with a receiving circuit. The driver circuit and the receiving circuit can be components of a sensor circuit arranged on the circuit card 3.

Housing 2 has a duct 9 passing through the transmitting coil 4 and the receiving coil 5 along their coincident axes of rotation. If the housing 2 is immersed in an electrically conductive medium 31, such surrounds the housing 2 and penetrates into the duct 9, so that a closed electrical current path passing through the two coils 4, 5 can form in the medium 9, when the transmitting coil 4 is excited with an alternating voltage, as explained above.

Figure 1D:
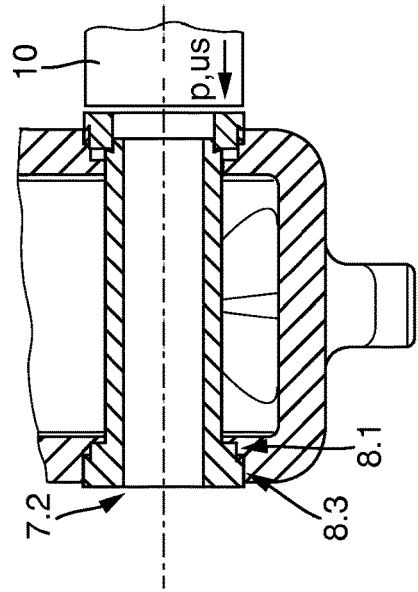
Figure 1E:
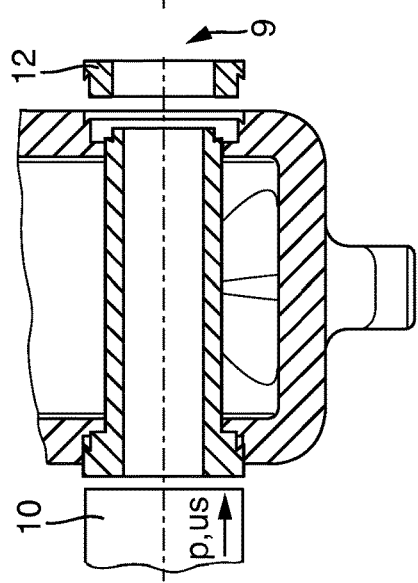

The sensor module 1 can be produced in the following manner: The circuit card 3, populated with the transmitting coil 4, the receiving coil 5 and, in given cases, additional circuit parts, is placed in the housing 2 in a first step (FIG. 1*b*). The transmitting coil 4 and the receiving coil 5 are so arranged on the circuit card 3 that they surround an opening 3*a* (drawn dashed) in the circuit card 3. Housing 2 can be manufactured, for example, by means of an injection molding method. Housing 2 includes two mutually opposing openings 7.1, 7.2, which align with the opening 3*a* in the circuit card 3 surrounded by the toroidal coils 4, 5. A sleeve 6 is inserted through the opening 7.2 of the housing 2 and through the therewith aligned opening 3*a* in the circuit card 3 and out to the additional opening 7.1. Sleeve 6 includes a first end section 6.1 and a second end section 6.2, wherein the first end section 6.1 is inserted first into the housing 2. The first end section 6.1, thus, comes to rest in the first opening 7.1 and the second end section 6.2 comes to rest in the second opening 7.2. FIG. 1*d* shows the welded state of the second end section 6.2 with the second opening 7.2 (weld seams with reference characters 8.1 and 8.3). FIG. 1*e* shows the welded state of the first end section 6.1 with the first opening 7.1 (welded seams with reference characters 8.2 and 8.4). For welding the first end section 6.1 with the housing 2, a counterpart 12 is inserted into the opening 7.1 and welded with the first end section 6.1 and the housing 2. In this way, the duct 9 extending axially relative to the shared rotational axis of the transmitting and receiving coils 4, 5 is completed. In measurement operation, medium 31 flows through duct 9.

After the mentioned welding procedures (see below), the welded seams 8.1, 8.2, 8.3, 8.4 are reworked, wherein possibly elevated particles are removed by machining. Since sleeve 6 serves in the case of an inductive conductivity sensor 1 for guiding a liquid medium through the duct 9, the radii of the sleeve 6 in the end regions 6.1, 6.2 are rounded toward the duct 9. These roundings extend, in such case, externally inwardly toward the duct 9 and improve the flow of the medium 31 flowing through the duct 9.

Both housing 2 as well as also sleeve 6 and counterpart 12 comprise a partially crystalline, thermoplastic material, especially a polyether ketone, especially polyetheretherketone (PEEK) or glass fiber reinforced polyetheretherketone. Alternatively, housing 2, sleeve 6 and counterpart 12 comprise an amorphous thermoplastic, especially a polysulfone, especially polyphenylene sulfone (PPSU).

Sleeve 6 is welded with the housing 2 by means of ultrasonic welding. In this regard, a sonotrode 10 is applied in a first step on the side of the second end section 6.2. Compare FIG. 1*c*. FIGS. 2*a* and 2*b* are detailed views in the upper region respectively before and after the welding. In a second working step, the sonotrode 10 is applied on the side of the first end section 6.1. Compare FIG. 1*d* in this regard. For this, either the sonotrode or the workpiece is rotated. Preferably, the sonotrode 10 is fixed and in a preferred embodiment applied from above on the workpiece, which is oriented relative to the sonotrode as a function of the method step. FIGS. 2*a* and 2*b* show detailed views of the lower region respectively before and after welding.

Welding thus proceeds in the time sequence, first weld seam 8.1, third weld seam 8.3, second weld seam 8.2 and fourth weld seam 8.4, wherein the first weld seam 8.1 and third weld seam 8.3, respectively second weld seam 8.2 and fourth weld seam 8.4, are for a certain time simultaneously molten. Third weld seam 8.3 and fourth weld seam 8.4 are not absolutely required. In the following, however, it is assumed that four welds, two per end, are used.

FIG. 2 shows the respective geometries for the welded seams 8.1, 8.2, 8.3 and 8.4.

FIG. 2a shows the sleeve 6 before the welding process and FIG. 2b shows the sleeve 6 after the welding process. The upper parts of the figures show the second end region 6.2, while the lower parts of the figures show the first end region 6.1 of the sleeve 6, in each case with the respective sections of the housing 2.

Shear joints are used for forming the seam geometry. The shear joint provides a sealed weld and is embodied as a step with very little contact area. This small area and the resulting high energy flow bring about a rapid melting. The sliding of the two melt surfaces relative to one another prevents hollow locations and air contact. In general, a homogeneous, tightly sealed connection is obtained.

As already mentioned the welding includes at least two welds 8.1 and 8.2. Preferably, however, there are four welds 8.1, 8.2, 8.3 and 8.4. Also, embodiments with three welds 8.1, 8.2 and 8.3, respectively welds 8.1, 8.2 and 8.4, provide other options. In an additional embodiment, the welding includes the welds 8.3 and 8.4.

A shear joint is used for the first weld seam 8.1. For forming the shear joint, the housing 2 includes a first wedge shaped profile 2.1, and the sleeve 6 a first planar area 6.3 corresponding to the first wedge shaped profile 2.1, wherein the occurring shear joint forms the first weld seam 8.1.

The housing 2 further includes a first concentrator 11.1, and the first concentrator 11.1 serves for forming the optional third weld seam 8.3 with a first inclined area 6.4 of the sleeve 6. "Inclined" in this connection means inclined in the cross section relative to the direction of introduction.

For forming the first weld seam 8.1 and the third weld seam 8.3, the sonotrode 10 is thus applied on the side of the second end section 6.2.

The first concentrator 11.1 as well as, in given cases, the second concentrator 11.2 and third concentrator 6.5 (see below) comprise a V-shaped profile having an acute angle between 90° and 60°, a triangular profile, a rectangular profile or a half round profile. Because of this profile, the concentrator can function also as an energy director. This geometry effects an initial, line shaped contact. The result is a very concentrated introduction of the ultrasonic energy and therewith a rapid heating and melting of the material.

The weld seam is nevertheless embodied as a shear joint, since the two portions to be welded slide into one another and form a medium excluding connection. There are different options for terminating the welding process, for instance, after expiration of a constant time, after travel of a constant path, after reaching of a certain point, after consumption of a predetermined amount of energy, after a predetermined power or a combination of all of these. Preferably, a constant path welding is used, i.e. the two components always melt equally far into one another. During welding, the sonotrode 10 exerts a defined pressure p with a certain ultrasonic energy US on the sleeve 6, respectively the counterpart 12. Welding is at room temperature.

A shear joint is used for the second weld seam 8.2. For forming the shear joint, the housing 2 includes a second wedge shaped profile 2.2. For forming the shear joint, the sleeve 6 further includes a third wedge shaped profile 6.5. The first end section 6.1 of the sleeve 6 is welded with the housing 2 and a counterpart 12 introduced into the first opening 7.1. Counterpart 12 includes a second planar area 12.1 corresponding to the second wedge shaped profile 2.2 and to the third wedge shaped profile 6.5, wherein the occurring shear joint forms the second weld seam 8.2. The weld seam 8.2 includes, thus, two subsections, which are both labeled with the reference character 8.2.

A shear joint is likewise used for the optional fourth weld seam 8.4. For forming the shear joint, the housing 2 includes a second concentrator 11.2 and the sleeve includes a third concentrator 6.5. The second concentrator 11.2 and the third concentrator 6.5 serve for forming the fourth weld seam 8.4 with a second inclined area 12.2 and a third inclined area 12.2 of the counterpart 12. "Inclined" in this connection means inclined in the cross section relative to the direction of introduction. The fourth weld seam 8.4 includes thus two subsections, which are here labeled with the same reference character 8.4.

For forming the second weld seam 8.2 and the fourth weld seam 8.4, the sonotrode 10 is thus applied on the side of the first end section 6.1.

Figure 3:
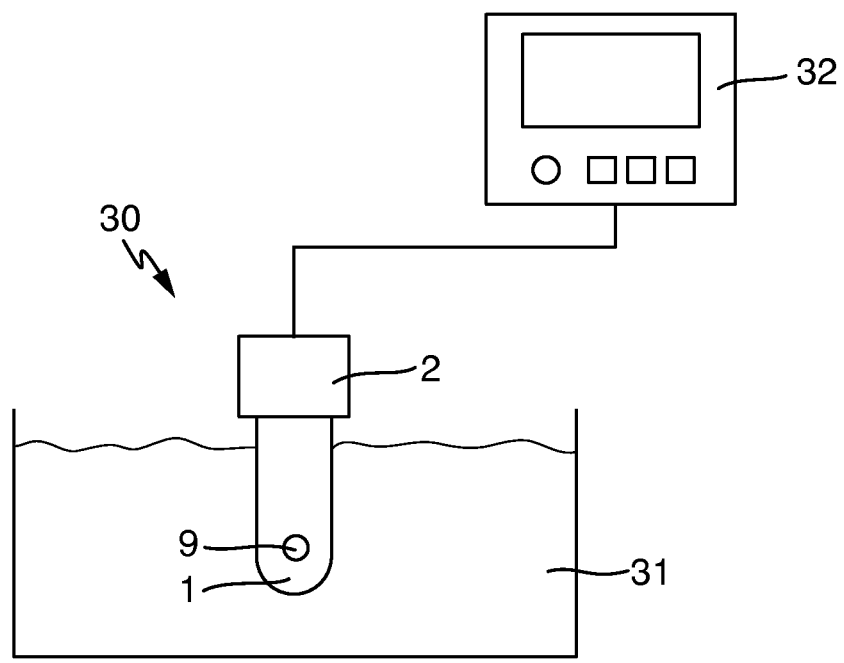
FIG. 3 shows the conductivity sensor in measurement operation.

FIG. 3 shows schematically a conductivity sensor 30 with a housing module 1 for immersion in a medium 31. Accommodated in the housing module 1 are the transmitting and receiving coils, as well as, in given cases, at least parts of the driver circuit exciting the transmitting coil with an alternating voltage and at least parts of the receiving circuit connected with the receiving coil and serving for registering and conditioning a signal induced in the receiving coil and dependent on the conductivity of the medium 31. The housing module 1 forms a duct 9 passing through the coils contained in the housing module 1. Medium 31 flows through duct 9, when the housing module 1 is immersed in the medium 31, such as shown in FIG. 3. Medium 31 can be located in a container, especially in a pipe or a reaction container, in a production plant. The conductivity sensor 30 is then held in a retractable assembly integrated in the pipe, respectively container, wall and inserted into the medium 31 contained in the pipe or container.

The sensor circuit contained in the housing module 1 is connected via a cable connection with a superordinated unit, in the present example with a measurement transmitter 32. The superordinated unit can also be a computer or a programmable logic controller. The connection between the conductivity sensor 30 and the superordinated unit can also be a wireless connection. In this case, the superordinated unit can also be a portable device, especially also an Internet—or radio capable telephone, such as e.g. a smart phone. The superordinated unit serves for supplying the sensor—and the driver circuit with energy, as well as for registering and additional processing, especially also for display, of measured values registered by the conductivity sensor 30.

The conductivity sensor 30 is connected, for instance, via a cable, for instance, via a galvanically isolated interface, especially an inductive interface, with a measurement transmitter 32. The measurement transmitter is, in turn, connected via a bus connection, such as Fieldbus Foundation, ModBus, HART or like bus connection, to a control system. Alternatively, the conductivity sensor can also be directly connected via a bus connection to a control system.

The invention claimed is:

1. A method for manufacturing an inductive conductivity sensor, the method comprising:
providing a housing including a first opening and a second opening, a circuit board including coils and an opening through the circuit board, a sleeve including a first end section and a second end section, and a counterpart, wherein the coils of the circuit board are disposed on opposing sides of the circuit board surrounding the opening;

inserting the circuit board with the coils into the housing such that the first opening of the housing, the second opening of the housing and the opening of the circuit board are aligned;

inserting the sleeve into the housing through the second opening of the housing and through the opening of the circuit board to the first opening;

inserting the counterpart into the first opening until the counterpart contacts the housing and/or the first end section of the sleeve; and welding the sleeve to the housing by ultrasonic welding using a sonotrode, wherein the first end section of the sleeve is welded to the housing and to the counterpart inserted into the first opening.

2. The method as claimed in claim 1, wherein:
a shear joint is used for forming a seam geometry of a first weld seam;
the housing includes a first wedge shaped profile for forming the first weld seam in a region of the second end section with a first planar area on the sleeve; and
the sonotrode is applied on the side of the second end section.

3. The method as claimed in claim 2, wherein:
a shear joint is used for forming a seam geometry of a second weld seam;
the housing includes a second wedge shaped profile;
the sleeve includes a third wedge shaped profile; and
the second wedge shaped profile and the third wedge shaped profile enable forming the second weld seam in a region of the first end section with a second planar area on the counterpart; and
the sonotrode is applied on the side of the first end section.

4. The method as claimed in claim 3, wherein:
a shear joint is used for forming a seam geometry of a third weld seam;
the housing includes a first concentrator, structured for forming the third weld seam in a region of the second end section with an inclined area of the sleeve; and
the sonotrode is applied on the side of the second end section.

5. The method as claimed in claim 4, wherein:
a shear joint is used for forming a seam geometry of a fourth weld seam;
the housing includes a second concentrator and the sleeve includes a third concentrator;
the second concentrator and the third concentrator facilitate forming the fourth weld seam in a region of the first end section with at least a first inclined area and a second inclined area of the counterpart; and
the sonotrode is applied on the side of the first end section.

6. The method as claimed in claim 5, wherein:
at least one concentrator has a V-shaped profile with an acute angle between 90° and 60°, a triangular profile, a rectangular profile or a half round profile.

7. The method according to claim 5, wherein:
the welding proceeds in a time sequence as follows: first weld seam, third weld seam, second weld seam, fourth weld seam; and
the first weld seam and the third weld seam, respectively the second weld seam and the fourth weld seam, are for a certain time simultaneously molten.

8. The method as claimed in claim 1, wherein:
the welding occurs at room temperature.

9. The method as claimed in claim 1, wherein:
the sleeve welded with the housing is further worked in the first end region and/or in the second end region.

10. An inductive conductivity sensor, wherein:
the inductive conductivity sensor is produced according to a method as defined in claim 1.

11. The inductive conductivity sensor as claimed in claim 10, wherein:
the housing, the sleeve and the counterpart comprise a partially crystalline thermoplastic.

12. The inductive conductivity sensor as claimed in claim 10, wherein:
the housing, the sleeve and the counterpart comprise an amorphous thermoplastic.

13. The inductive conductivity sensor as claimed in claim 10, wherein:
the second end section includes at least a first weld seam, and the first end section includes at least a second weld seam.

14. The inductive conductivity sensor as claimed in claim 13, wherein:
the second end section includes supplementally at least a third weld seam, and the first end section includes supplementally at least a fourth weld seam.

15. The inductive conductivity sensor as claimed in claim 11, wherein:
the partially crystalline thermoplastic is polyether ketone or polyetheretherketone.

16. The inductive conductivity sensor as claimed in claim 12, wherein:
the amorphous thermoplastic is polysulfone or polyphenylene sulfone.

17. The method as claimed in claim 1 wherein:
the welding includes:
using a shear joint for forming a seam geometry of a weld seam, wherein the housing includes a wedge shaped profile and the sleeve includes a further wedge shaped profile, wherein the wedge shaped profile of the housing and the wedge shaped profile of the sleeve enable forming the weld seam in a region of the first end section with a planar area on the counterpart; and
applying the sonotrode on the side of the first end section.

18. The method as claimed in claim 17, wherein:
the welding further includes:
using a shear joint for forming a seam geometry of an additional weld seam, wherein the housing includes a concentrator and the sleeve includes a concentrator, wherein the concentrator of the housing and the concentrator of the sleeve facilitate forming the additional weld seam in a region of the first end section with at least a first inclined area and a second inclined area of the counterpart; and
applying the sonotrode on the side of the first end section.

19. The method as claimed in claim 18, wherein:
during the welding of the sleeve to the housing, the weld seam and the additional weld seem are for a certain time simultaneously molten.

* * * * *